US006655545B1

(12) United States Patent
Sonneborn

(10) Patent No.: US 6,655,545 B1
(45) Date of Patent: Dec. 2, 2003

(54) MEDICAL CODE SYSTEM

(76) Inventor: Jennifer Sonneborn, 3535 Old Mountain View Rd., Lafayette, CA (US) 94549

( * ) Notice: Subject to any disclaimer, the term of this patent is extended or adjusted under 35 U.S.C. 154(b) by 65 days.

(21) Appl. No.: 10/132,503

(22) Filed: Apr. 25, 2002

(51) Int. Cl.[7] ................................................. G07F 11/00
(52) U.S. Cl. ................................. 221/7; 221/9; 600/300
(58) Field of Search .............................. 221/2, 3, 7, 13, 221/9, 92, 129; 700/231, 237, 242, 213; 312/218, 215, 209; 600/300

(56) References Cited

U.S. PATENT DOCUMENTS

| | | |
|---|---|---|
| 4,790,610 A | 12/1988 | Welch et al. |
| 5,181,521 A | 1/1993 | Lemelson |
| 5,292,029 A | 3/1994 | Pearson |
| 5,687,717 A | 11/1997 | Halpern et al. |
| 6,011,999 A | 1/2000 | Holmes |
| 6,116,461 A | 9/2000 | Broadfield et al. |
| 6,477,442 B1 * | 11/2002 | Valerino, Sr. ............... 700/213 |

* cited by examiner

*Primary Examiner*—Kenneth W. Noland
(74) *Attorney, Agent, or Firm*—Jack Lo

(57) ABSTRACT

An improved emergency code cart (100) is provided. The cart contains a number of drawers (130), each containing medications (305, 310) and instruments (315) required for a particular code algorithm. The contents of each drawer are organized according to ACLS (American Cardiac Life Support) or other guidelines. The cart also contains a computer (175) which is programmed with ACLS algorithms or other guidelines which are the current standard of emergency patient care. The cart's computer monitors the patient's EKG, blood pressure, pulse oximetry, and other indicators, providing diagnostic information to the medical personnel in the code team. Upon select of a code algorithm, the computer provides prompts according to the algorithm, issues alarms when the algorithm is not followed, provides automatic synchronized cardioversion, prints an EKG rhythm strip, and documents all activities occurring in a code, including withdrawal, replacement, and use of medication and instruments.

29 Claims, 12 Drawing Sheets

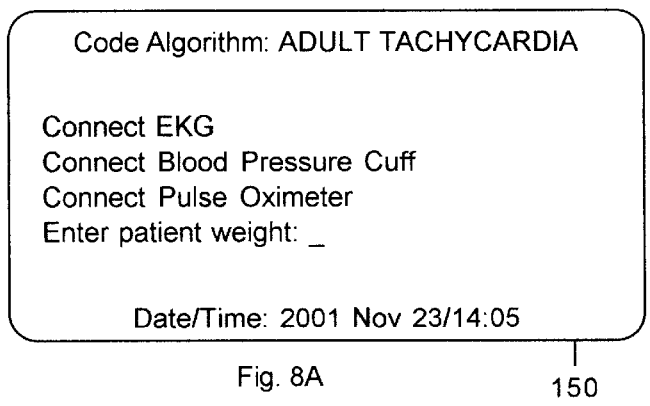
Fig. 8A    150
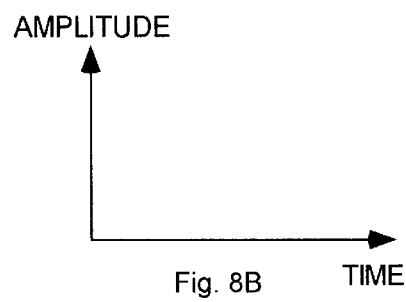
Fig. 8B
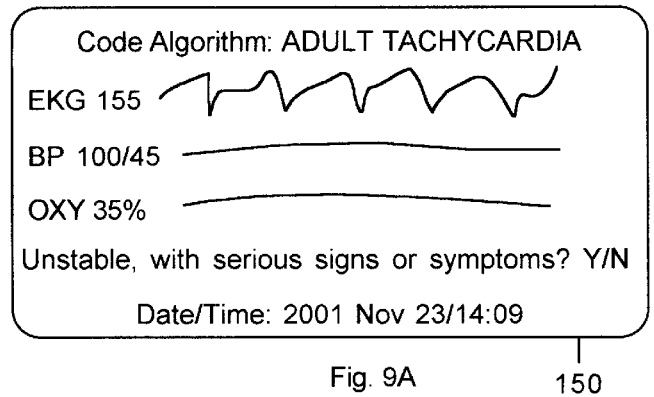
Fig. 9A    150
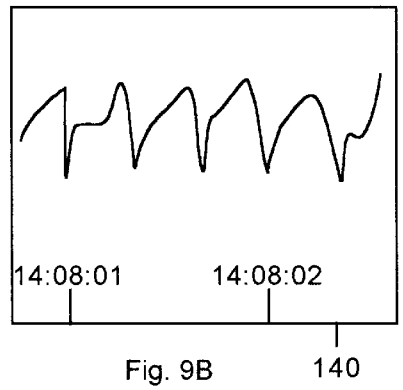
Fig. 9B    140
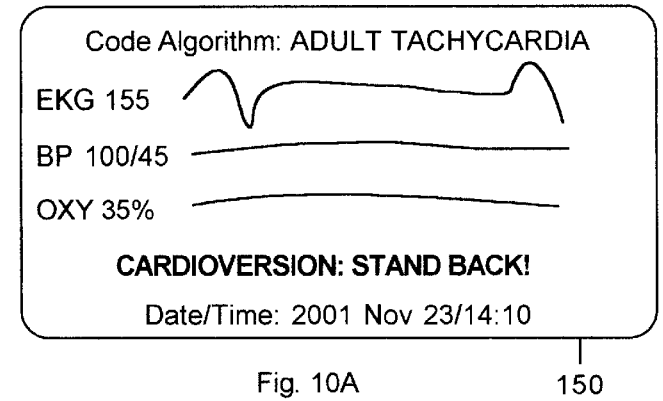
Fig. 10A    150
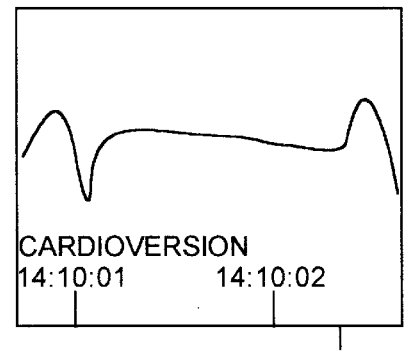
Fig. 10B    140

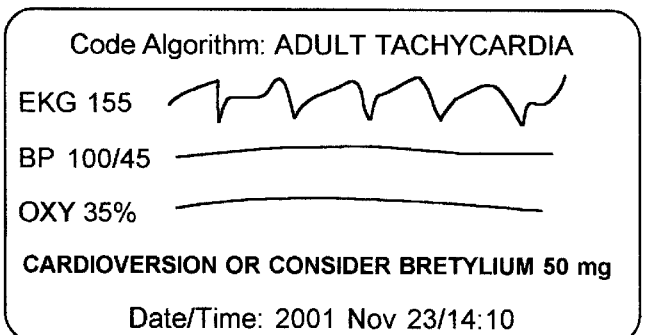
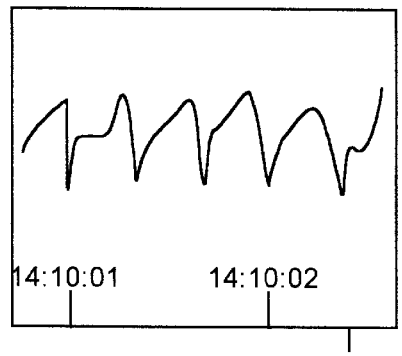
Fig. 11A    150      Fig. 11B    140
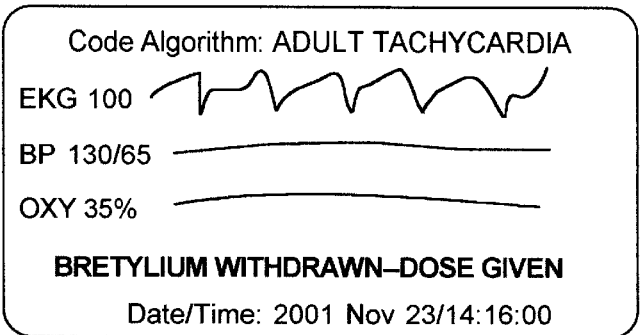
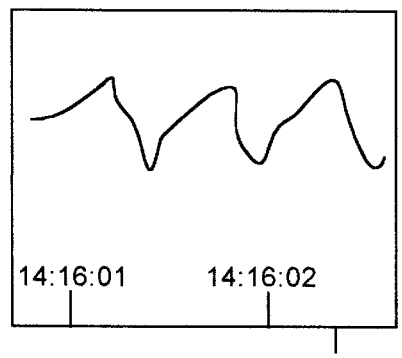
Fig. 12A    150      Fig. 12B    140
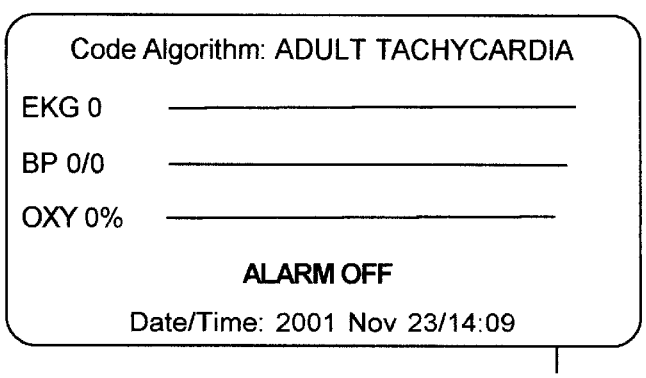
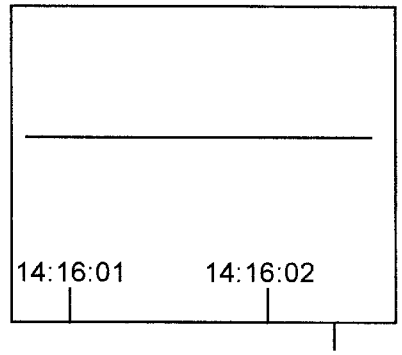
Fig. 13A    150      Fig. 13B    140

MEDICAL CODE SYSTEM

BACKGROUND

1. Field of Invention

This invention relates to hospital emergency carts, in particular to carts which contain medications and devices for use in life-threatening conditions.

2. Prior Art

In U.S. Pat. No. 6,116,461 (2000), Broadfield et al. teach a system and apparatus in which modular receptacles are filled with medications and transported to automatic dispensing machines for later retrieval and distribution. Memory chips, associated with a computer, store and maintain information about the contents of each receptacle, such as expiration dates of drugs and the like. An inventory of the receptacles' contents is automatically maintained as users access each receptacle.

In U.S. Pat. No. 6,011,999 (2000), Holmes teaches a dispensing apparatus for controlled dispensing of pharmaceutical and medical supplies which includes a cabinet having a plurality of drawers, each containing a plurality of receptacles. The receptacles have lockable lids which are unlocked under the control of an electronic processor. The processor prevents access to contents of the receptacles by unauthorized personnel. It also keeps an inventory of the contents of the cabinet.

Pearson, in U.S. Pat. No. 5,292,029 (1994), teaches a dispensing system in a mobile cart. The cart comprises a plurality of containers containing doctor-prescribed medications for individual patients. To dispense medication, a nurse enters a patient ID code into a microprocessor program, the program causes the microprocessor to actuate a mechanism which releases secured medication-dispensing units on the cart. The microprocessor records the time, date, and quantity of medication dispensed.

While each of these systems provides for the secure transport and delivery of medications, none provides a check or alarm against the possible misapplication or mistaken prescription of a drug. Further, none provides a check against established standards for dispensing of medications and apparatus, especially during a life-threatening emergency. Still further, none provides patient diagnostic feedback and guidance during a medical emergency.

When respiratory and circulatory processes are interrupted, prompt treatment directly correlates with optimal outcome for successful revival and minimization of neurological damage to the patient. In the past in hospitals, clinics, and some paramedic units, the traditional "code cart" came into use. The cart carries equipment needed to monitor activity of the heart, emergency medications, electrical defibrillator, and supplies and apparatus necessary to maintain respiratory function. Drawers in the cart typically contain supplies such as intravenous equipment, syringes, supplies for airway management, an electrocardiograph (EKG), a defibrillator equipped with EKG capability for cardioversion, and the like. The placement of supplies and equipment in a code cart often vary from one medical facility to another.

The cart is normally wheeled to a patient who is in a life-threatening medical condition, usually referred to as a "code". A group of hospital personnel remove various items from the cart as they are needed and administer them to the patient, usually under the direction of one person, i.e. a physician, who leads the code. This person calls out the recommended "interventions" that are needed at any point during the code. One member of the code team, the recorder, observes the code as it progresses and records all events related to the code. Other code team members identify and manage airway problems, give Cardio-Pulmonary Resuscitation (CPR) if required, maintain an intravenous (IV) site, and administer medications.

In the United States, codes are typically conducted according to the most recent Advanced Cardiac Life Support guidelines for standard care, issued by the American Heart Association. These guidelines are furnished in the form of algorithms. Each algorithm proceeds along established pathways of treatment for varied dysrhythmias, such as tachycardia, as the patient's clinical condition is affected. Numerous other algorithms exist, including the Asystole Treatment Algorithm, Bradycardia and Heart Block Algorithm, and the like. These algorithms apply to adults. Another group of algorithms applies to children, to address emergencies pertaining to pediatric patients.

At the start of a code, the proper algorithm is determined and may be used as a guide during the code. More than one algorithm may be used during the code, according to the patients' condition. At present, these guidelines are in written form, and also memorized by Advanced Cardiac Life Support (ACLS) caregivers as part of an over-all educational program.

The prior-art cart is adequate to convey medicines and apparatus to the patient. However, care of the patient is provided by a group of individuals. In this group effort, which is normally highly stressful for all concerned, it is possible for the correct focus of the code to be lost. For example, a medication may be removed form the cart and not given, given more than once, given at the wrong time, or otherwise be contraindicated.

Because of the rapid pace at which numerous events occur, the level of stress, the complicated nature of the work in progress, and the large volume of information which must be recorded, the recorder may have difficulty documenting the scenario accurately. For later examination of the recorder's record, it is important to note the time at which events occurred relative to the patient's condition. For example, the patient's heart rate or the quality of their pulse may change in response to an intervention. The timing of these and other events is essential in the proper documentation of the code. Due to the high volume of writing required in a short period of time, the margin of error in documentation is high. The recorder has several timepieces to choose from: a watch, a clock on the wall, the time stamp on an EKG record, and the like. If possible, a single source of the time of day should be used since all these sources will likely vary by several minutes. For example, the EKG monitor displays the time of its inner clock. If this is the official time record, then the reporter should use it to indicate the timing of drug deliveries which is generally different from other time sources available, such as a wrist watch or clock on the wall. However, the EKG record is often printed after the code, which makes it difficult or impossible to coordinate with the recorder's watch.

The overall effect is that prior-art carts being utilized today leave a large margin for human error in administering the appropriate treatment or medications, thus increasing the margin for injury to patients and the medical team. Medications are generally supplied in boxed packages containing glass vials or syringes with needles. These can be awkward and hazardous to assemble. In addition, the location of these items varies from one code cart to another, making it difficult to find them. This adds to the stress experienced by code personnel, increasing the risk of accidents during a code. This inefficient system contributes to slower response times in delivery of care.

SUMMARY

Accordingly, several objects and advantages of the invention are to provide an improved medical code cart system for dispensing medicines and medical equipment, with the addition of a check system of medications and equipment prior to use, to act as a safety mechanism for appropriateness for use. Other objects are to provide a computerized system which reduces human error, maintains a running inventory of the contents of the cart, provides information to a facility's restocking and billing departments, contains its own internal clock and calculator, optionally provides visible and audible alarms appropriate to various unsafe conditions, and provides diagnostic interplay with code team users to promote speed and accuracy in delivery of patient care. Further objects and advantages will become apparent from a consideration of the ensuing description and the accompanying drawings.

In accordance with the present invention, a computerized cart and method are provided which are programmed with Advanced Cardiac Life Support (ACLS) and perhaps additional algorithms to act as a guide throughout a given code. The cart's computer contains a calculator function for computing dosage amounts of medications, based on the patient's weight. Its programming also contains a continual diagnostic electrocardiogram function which will aid in the identification of shockable rhythms or ones requiring external pacing. Inputs are also provided from patient data by ancillary monitoring equipment, including ongoing blood pressure monitoring, and other diagnostic equipment. Subjective data on the patient's condition is logged in by the team recorder. The cart's computer analyzes and records data from these sources and provides guidance through the code algorithm, issuing alarms and making suggestions when appropriate. All information about the code is displayed on the computer's monitor screen. A permanent record of progress through the code is maintained, indicating the withdrawal of items from the cart, the times at which interventions occur, and the resulting condition of the patient, as evidenced by EKG, oximeter, blood pressure, and other readings. This record can be downloaded from the computer, saved to disk, and printed.

The contents of the cart are organized in a manner which reflects current ACLS guidelines drawer by drawer, in a left-to-right fashion. When the drawer for a code algorithm is opened, electrical switches detect the removal of medications and medical equipment from the cart and convey this information to the cart's computer for entry into a permanent record. A button associated with each medication is pressed as the medication is given to the patient. This information is also entered into the record by the cart's computer. If a medication or intervention which is not indicated by the algorithm is withdrawn from the cart, the cart's computer provides a visual or audible alarm, or both, to alert the individuals conducting the code that the algorithm is not being followed. The system also prompts the code team, suggesting certain actions as appropriate, based on the current algorithm and the patient's condition without locking out the physician's choice of action. All interventions, recommended or not or done by a physician's choice are recorded. The individuals conducting the code can still give the medication in question, and its administration will be logged by the recorder. Pre-mixed or easy-to-mix medications are packaged ready-for-use. Needle-less syringes contain predetermined quantities of medications.

BRIEF DESCRIPTION OF THE DRAWINGS

FIG. 8A shows the appearance of the cart computer's monitor screen and the EKG rhythm strip.

FIG. 8B shows the appearance of the cart computer's monitor screen and the EKG rhythm strip.

FIG. 9A shows the appearance of the cart computer's monitor screen and the EKG rhythm strip.

FIG. 9B shows the appearance of the cart computer's monitor screen and the EKG rhythm strip.

FIG. 10A shows the appearance of the cart computer's monitor screen and the EKG rhythm strip.

FIG. 10B shows the appearance of the cart computer's monitor screen and the EKG rhythm strip.

FIG. 11A shows the appearance of the cart computer's monitor screen and the EKG rhythm strip.

FIG. 11B shows the appearance of the cart computer's monitor screen and the EKG rhythm strip.

FIG. 12A shows the appearance of the cart computer's monitor screen and the EKG rhythm strip.

FIG. 12B shows the appearance of the cart computer's monitor screen and the EKG rhythm strip.

FIG. 13A shows the appearance of the cart computer's monitor screen and the EKG rhythm strip.

FIG. 13B shows the appearance of the cart computer's monitor screen and the EKG rhythm strip.

Figure 1:
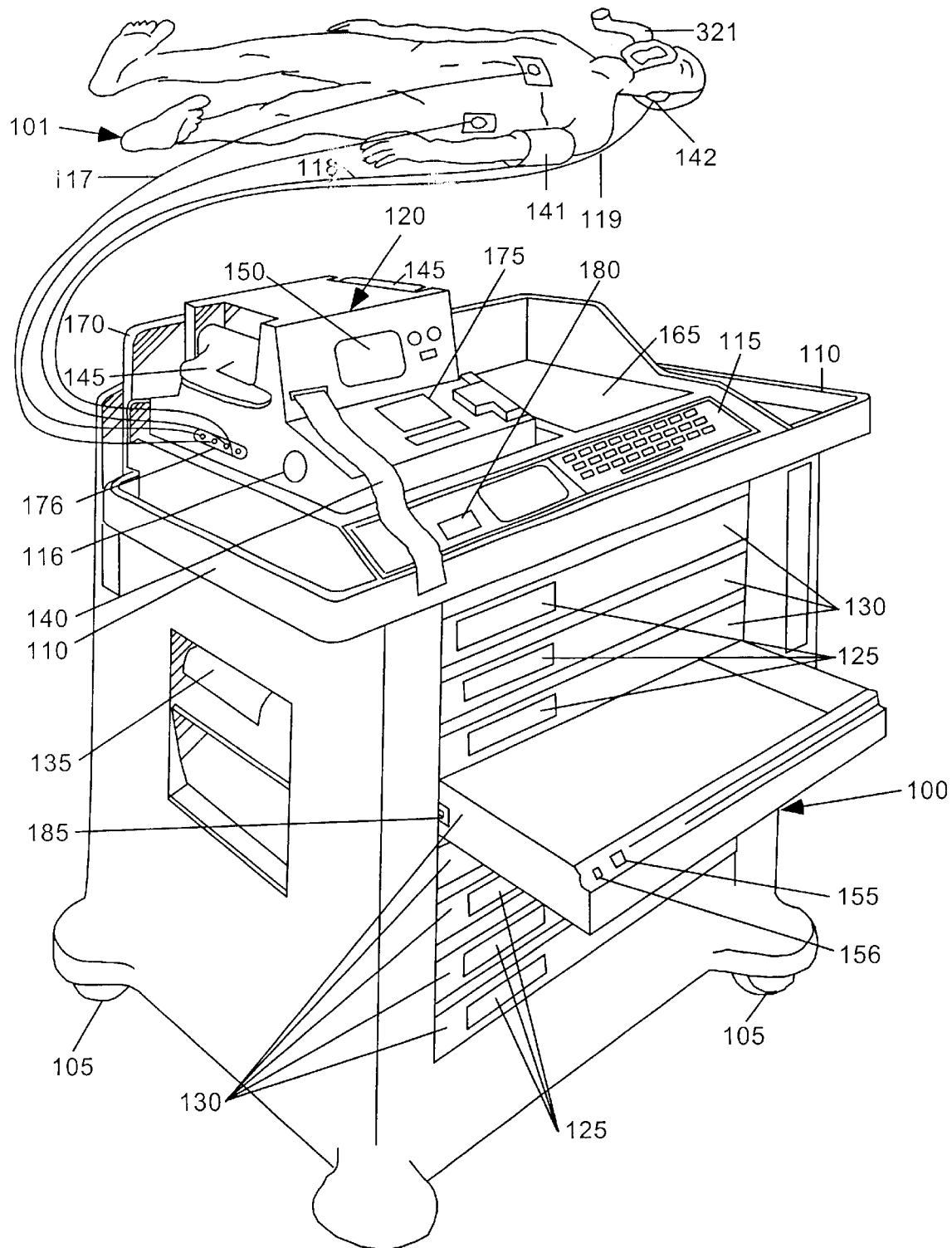
FIG. 1 is a front perspective view of a medical code cart system and interconnections to a patient, according to the present invention.

| DRAWING REFERENCE NUMERALS | | | |
|---|---|---|---|
| 100 | Cart | 170 | Back board |
| 101 | Patient | 175 | Computer |
| 105 | Wheel | 176 | Connector |
| 110 | Handle | 180 | Power monitor indicator |
| 115 | Keyboard | 185 | Switch |
| 116 | Loudspeaker | 200 | Oxygen tank |

-continued

DRAWING REFERENCE NUMERALS

| | | | |
|---|---|---|---|
| 117 | Leads | 205 | Power connector |
| 118 | Tubing | 210 | UPS |
| 119 | Cable | 300 | Compartments |
| 120 | Table top | 305 | Medication |
| 125 | Labels | 310 | Medication or apparatus |
| 130 | Drawers | 315 | Syringe |
| 135 | Printed record | 320 | Tubing or EKG wires |
| 140 | EKG rhythm strip | 321 | Airway appliance |
| 141 | Blood pressure cuff | 325 | Label |
| 142 | Pulse oximeter sensor | 400 | Optical sensor |
| 145 | Defibrillator paddle | 405 | Emitted light beam |
| 150 | Monitor screen | 410 | Reflected light beam |
| 155 | Switch | 500 | Electrical contact |
| 156 | Light | 505 | Electrical contact |
| 165 | Writing space | | |

DETAILED DESCRIPTION OF THE DRAWINGS

FIG. 1 is a front perspective view of a medical code housing or cart 100 according to the present invention. Cart 100 is made of a strong, sturdy material such as metal, reinforced plastic, or wood. Wheels 105 swivel in their mounts (not shown) permitting universal maneuverability. They can also be locked by locking mechanisms (not shown) to prevent movement of the cart. Handles 110 on both sides of cart 100 allow cart 100 to be pushed or pulled, as required. Alternatively, system may comprise a non-rolling housing such as a cabinet.

Table top area 120 contains a computer 175 which has a display screen 150, an input device such as a keyboard 115, a sonic generator or loudspeaker 116 which emits alarms and other sounds such as speech as required to indicate progress through the computer's program, and a printer (not shown) which prints a permanent record of the chronology of the code on paper 135. Table top area 120 also contains a convenient space 165 for writing. Computer 175 also has a computer network connection (not shown), and one or more storage devices such as a floppy disk, CD ROM, DVD ROM, or portable disk drive, for ease of transporting and storing data.

The storage device (not shown) of computer 175, such as a hard disk, contains numerous ACLS algorithms and other emergency guidelines, ready to be activated. A program in the storage device of computer 175 also computes medication dosages based on the patient's weight, and has lock-in and lock-out features which are pre-programmed to alert the code team to possible allergies and physician preferences. Additional computer functions include a real-time clock, and audible and visual prompts.

Computer 175 also contains an electrocardiograph (EKG), a defibrillator, and interfaces to a pulse-oximeter sensor 142, and an automatic blood pressure monitor cuff 141. Connections to sensing apparatus on patient 101 are made via connector 176. The EKG connects to patient 101 through leads 117. Blood pressure cuff 141 connects to computer 175 via tubing 118. Pulse oximeter sensor 142 connects to computer 175 through cable 119. The defibrillator contained in computer 175 can be internal to the cart's computer system, or external. If it is internal, leads 117 which are used for EKG input, can also be used for defibrillation. Alternatively, instead of using EKG leads 117 to deliver a defibrillating shock, paddles 145 are used.

A "rhythm strip" 140 printed by computer 175 documents the EKG of patient 101 during the code. This is a printed strip that includes time marks indicating when each intervention takes place, and shows the response of patient 101 to these interventions. Normally, just the chronological sequences of these events need to be documented, but the entire code can be recalled from computer 175 if desired. Strip 140 can be very long, on the order of ten or more meters for a typical code, and contains a longer history of EKG events than can be displayed at one time on monitor screen 150.

Figure 3:
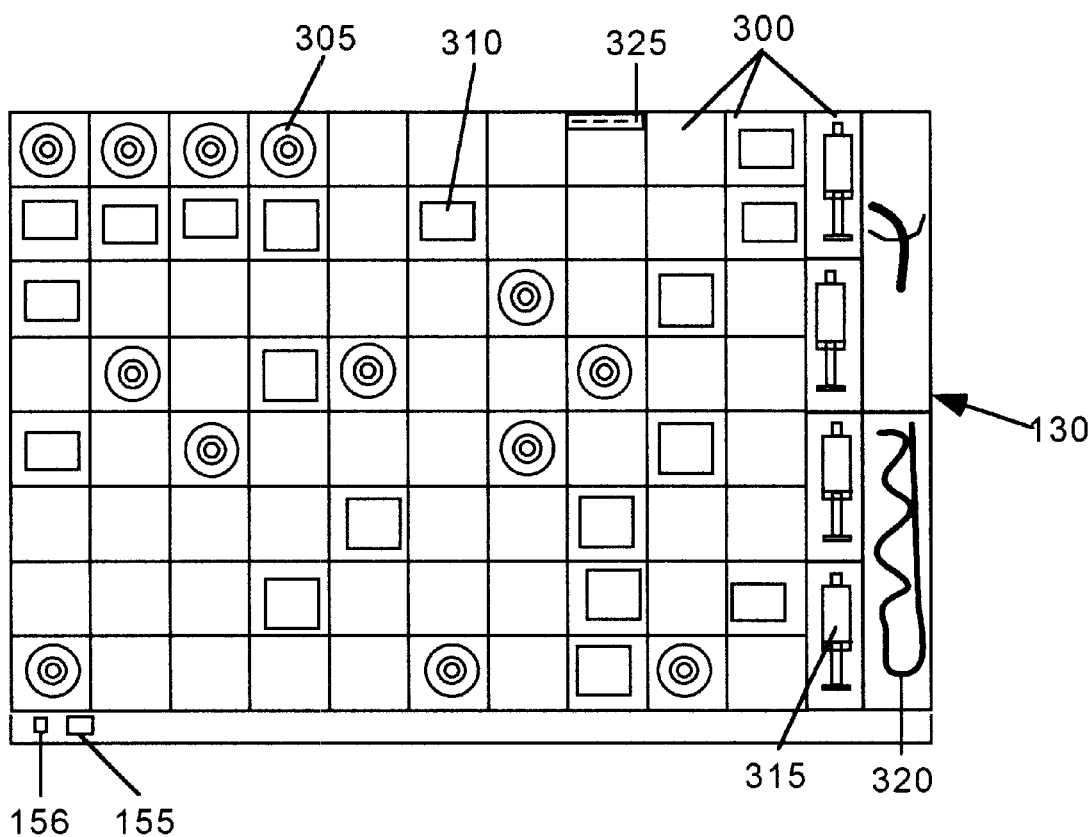
FIG. 3 is a top view of a drawer.

Each drawer 130 in cart 100 contains the materials required for a particular code algorithm, including medications 305, 310, 315 and medical equipment 320 (FIG. 3). Their placement is arranged in drawer 130 according to ACLS guidelines. Each drawer 130 also has a label 125 which is printed with a graphic symbol representative of a particular code or a list of the contents of that drawer.

Each drawer 130 further contains a supply location indicator lamp 156 and a supply usage recording switch 155 connected to computer 175, for use by the recorder. Additional sensors, discussed below, within each drawer detect the removal of the contents of a drawer. Each drawer 130 optionally contains a open-drawer detection switch 185 which is activated when the drawer is opened. If present, switch 185 is also connected to computer 175.

Figure 14:
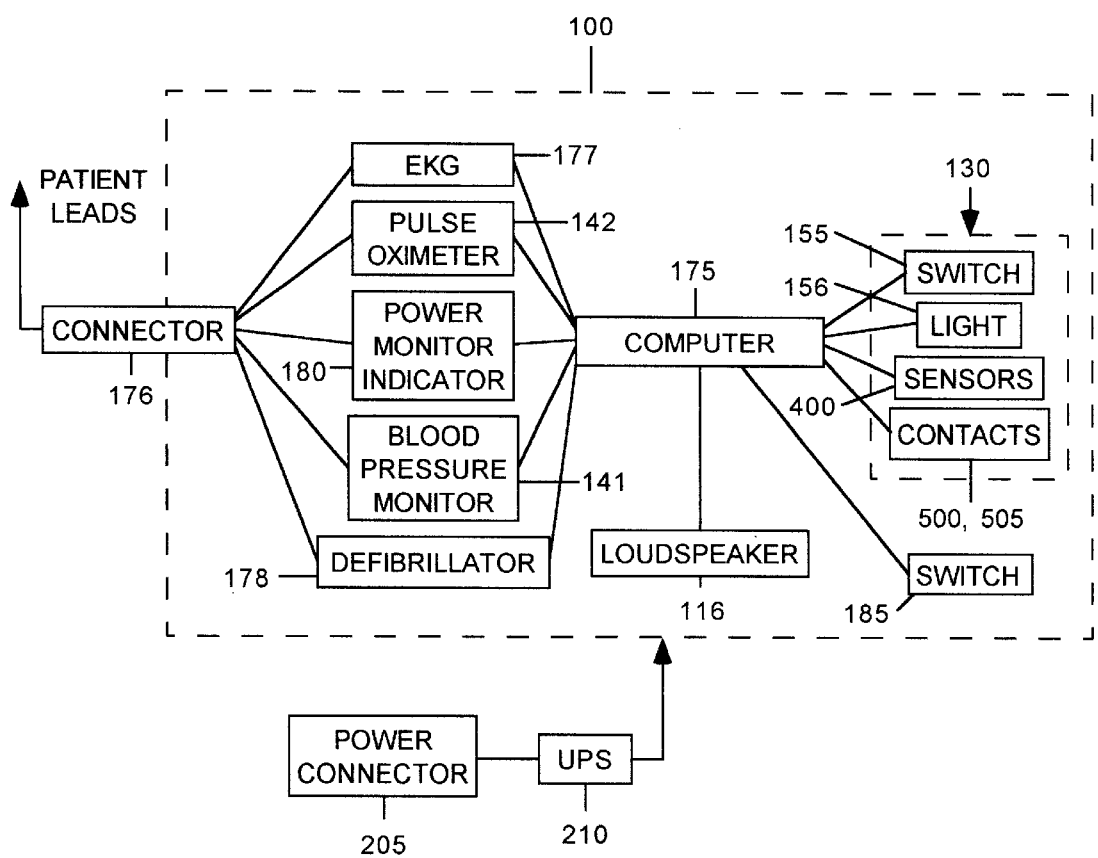
FIG. 14 is an electrical block diagram of the code cart system.

A block diagram of the code cart system is shown in FIG. 14. Electrical power is supplied to UPS 210 through connector 205. UPS 210 powers all devices contained within cart 100, including EKG 177, defibrillator 178, power monitor indicator 180, blood pressure monitor 141, and computer 175. Loudspeaker 116 is powered by computer 175. Connections to the patient are made through connector 176. Light 155 is also powered by computer 175. Switches 155 and 185, sensors 400 and contacts 500 and 505 are connected to computer 175 which senses their operation.

Figure 2:
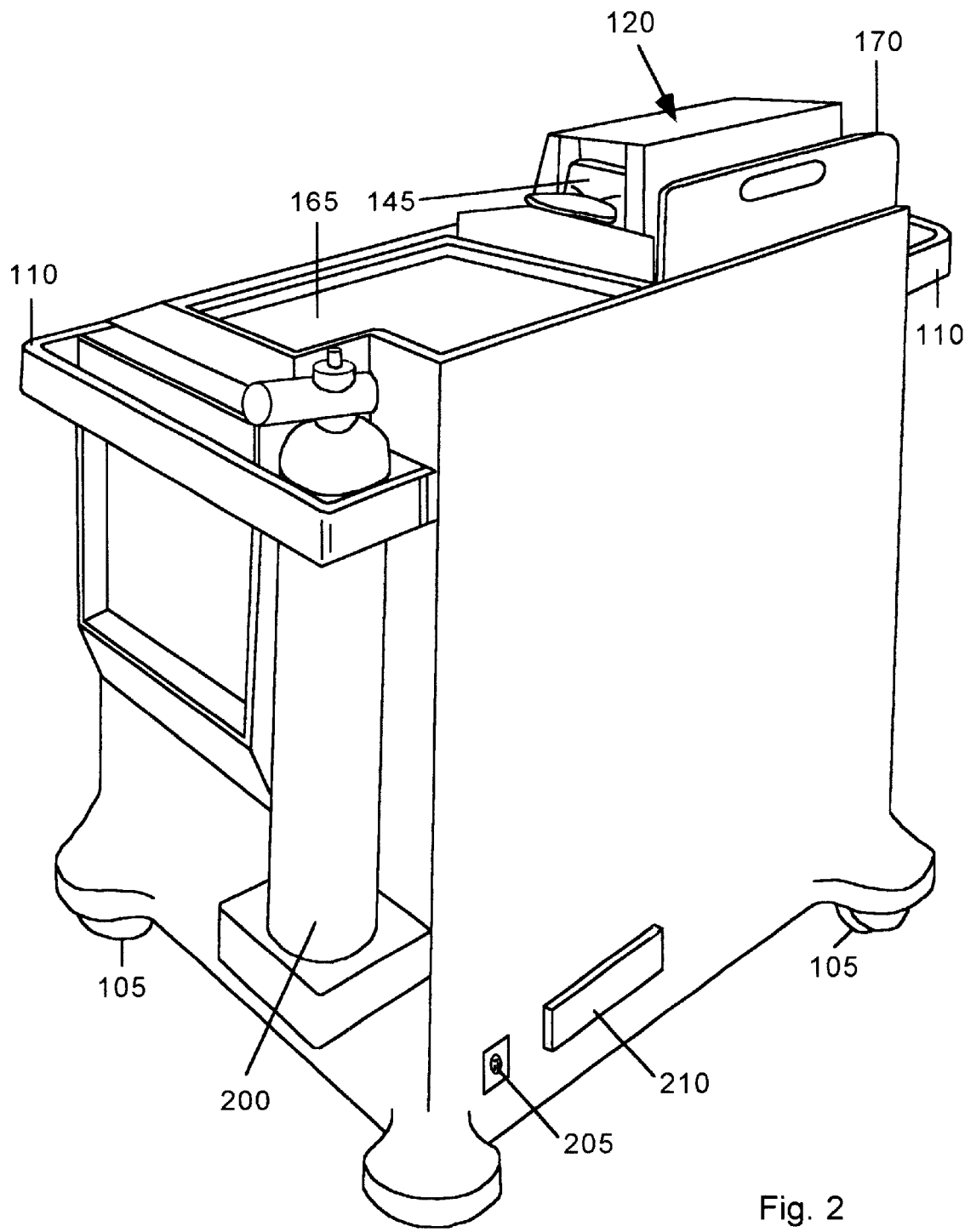
FIG. 2 is a rear perspective view of the cart of FIG. 1.

FIG. 2 is a perspective view of the back side of cart 100. An oxygen tank 200 is provided to assist ventilation of patient 101 (FIG. 1). A power supply connector 205 connects to a retractable power cord (not shown) which is normally plugged into a red hospital outlet. The cord is retracted for safety when not in use to prevent entanglement and falls. Red outlets are connected to an auxiliary power supply in the event that there is a primary power failure. Cart 100 also contains an Uninterruptible Power Supply (UPS) 210. UPS 210 contains batteries which keep all functions of cart 100 operational for brief periods of time, up to 60 minutes, when the primary source of power is disconnected. This occurs when cart 100 is moved from its storage location to a patient 101, for example. Once at the patient's bedside, the cart can again be plugged into a red outlet, if desired. A power status indicator 180 (FIG. 1) indicates the charge condition of the batteries in the UPS at all times. If a cart's batteries are unable to hold a charge, this is so indicated by indicator 180 and the batteries or the entire cart can be replaced so that a fully-functional unit is always available.

FIG. 3 is a top view of a typical drawer 130 in cart 100. Drawer 130 contains a plurality of compartments 300 of various sizes. Compartments 300 typically hold vials 305, containers 310, pre-filled, needle-less syringes 315, tubing and appliances 320, airway appliances 321, and the like, in a prescribed order, as specified by ACLS or other guidelines. Compartments 300 can have labels 325, if required. Arrangements are subject to events occurring within guidelines and may be rearranged and software updated upon events occurring.

Drawer 130 contains sensors in each compartment 300 which are arranged to signal computer 175 (FIG. 1) when the contents 305, 310, etc. of a drawer 130 are withdrawn. Typical sensors are shown in FIGS. 4A and 4B, and 5A and 5B.

Figures 4A, 4B:
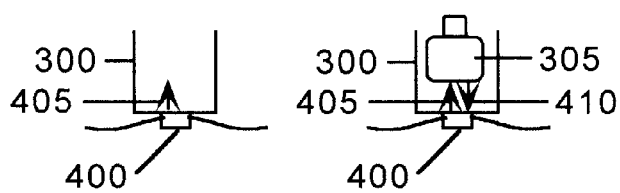
FIG. 4 is a side view of an optical sensor in a compartment in the drawer of FIG. 3.

In FIG. 4A, sensor 400 is a photo-emitter-photo-detector combination. A typical sensor of this type is the model OBP742, made by Optek Technology, Inc. of Carrollton, Tex. U.S.A. When compartment 300 is empty, as in FIG. 4A, light 405 is emitted by sensor 400 and escapes into the void above. In this case, the output of sensor 400 is sensed by computer 175 (FIG. 1) as a logical "0", indicating the absence of contents in compartment 300. In FIG. 4B, when an object such as vial 305 rests on the bottom of compartment 300, light 405 is reflected as beam 410 back into sensor 400 and detected by the internal photo-detector. In this case, the output of sensor 400 is sensed by computer 175 as a logical "1", indicating the presence of an object such as vial 305. Sensors 400 are designed such that objects which are detected must be located within a small distance, such as on the order of 1 cm. Objects which are at a greater distance are not detected. This prevents sensor 400 from erroneously detecting objects which lie outside the confines of compartment 300.

Figures 5A, 5B:
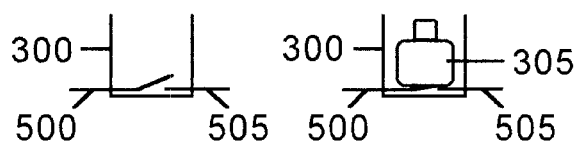
FIG. 5 is a side view of an electrical switch in a compartment in the drawer of FIG. 3.

A simpler sensor is shown in FIG. 5A. Electrical contacts 500 and 505 are normally not in contact. Contact 500 is normally biased away from contact 505. In this case, an open circuit, or logical "0" is detected by circuitry (not shown) associated with computer 175 (FIG. 1), indicating the absence of contents in compartment 300. In FIG. 5B, when an object such as vial 305 rests on top of contact 500, its weight causes contact 500 to bend downward and come into contact with contact 505, closing the circuit between contacts 500 and 505. In this case, a logical "1" is detected by circuitry associated with computer 175, indicating the presence of an object such as vial 305 in compartment 300.

If contents 305, 310, etc. are replaced in compartment 300, sensor 400 or 500 will also indicate this to computer 175.

By communicating with sensors 400 or 500, computer 175 has the ability to check the removed medication or equipment against the ACLS or other algorithm for a particular code in progress. When a medication or piece of equipment 305, 310, 315, etc. is removed from drawer 130, computer 175 notes this removal and checks it against the current algorithm. If the medication or apparatus is not indicated by the code algorithm, computer 175 issues an alarm. The alarm can be visible on the monitor screen of computer 175, or at times audible. Whether the alarm is visible or audible depends on the importance of the alarming condition. If the medication or apparatus is replaced in its original location after such an alarm, computer 175 deletes the removal from the record. If the medication or apparatus is anticipated as the next step on the code algorithm, computer 175 energizes a lamp 156 on drawer 130. When the medication or equipment is actually used on patient 101, the recorder presses button 155, signaling computer 175, and this information is noted on the printed record.

When there is no code in progress, cart 100 (FIG. 1) operates in "standby mode" and is parked at a convenient location and plugged into a main power source (not shown) via an electrical cable (not shown) which is connected to power connector 205 (FIG. 2). This source is normally a red electrical outlet, indicating that the medical facility's emergency generator will provide power to this outlet in the event of an external power failure. UPS 210 is connected to connector 205 and receives power whenever power is delivered to connector 205. Batteries (not shown) in UPS 210 are kept in a fully-charged condition when the cart is in standby mode.

During a code, computer 175 analyzes data, provides diagnostic information to the code team, proposes code algorithms, monitors progress through the current algorithm, makes suggestions based on the patient's condition, issues alarms, monitors removal and replacement of contents from cart 100, and records all data and events as a function of time. Various computer functions include:

1. EKG: During a code, the patient's EKG is continuously monitored and displayed on display 150 and printed on rhythm strip 140. Each intervention is also noted on display 150 and strip 140 to enable the code team to evaluate the patient's condition.

2. Defibrillation: An "intelligent" defibrillator is contained in computer 175. Exemplar defibrillators are manufactured by Medtronic Physio-Control, of Redmond, Wash., U.S.A., and sold under the mark "LIFEPAK". When the defibrillator is enabled, defibrillating shocks are applied to patient 101 via EKG leads 117 or paddles 145. Computer 175 analyzes the patient's EKG and determines the proper time in the patient's heart rhythm to apply a defibrillating shock. This action is called "synchronized cardioversion". Prior to automatic application of the defibrillation voltage, computer 175 issues a verbal command to the code team via loudspeaker 116: "CLEAR!" or "STAND BACK".

3. Blood Pressure: The patient's blood pressure is measured at programmed intervals using an automatic blood pressure meter contained within computer 175. This meter receives data from blood pressure cuff 141 on patient 101.

4. Pulse Oximetry: The oxygenation level in the patient's blood can be continuously monitored and recorded by pulse oximeter 142, also a component within computer 175.

5. Interventions: The time at which each intervention occurs is recorded in the storage device of computer 175.

Figure 6A:
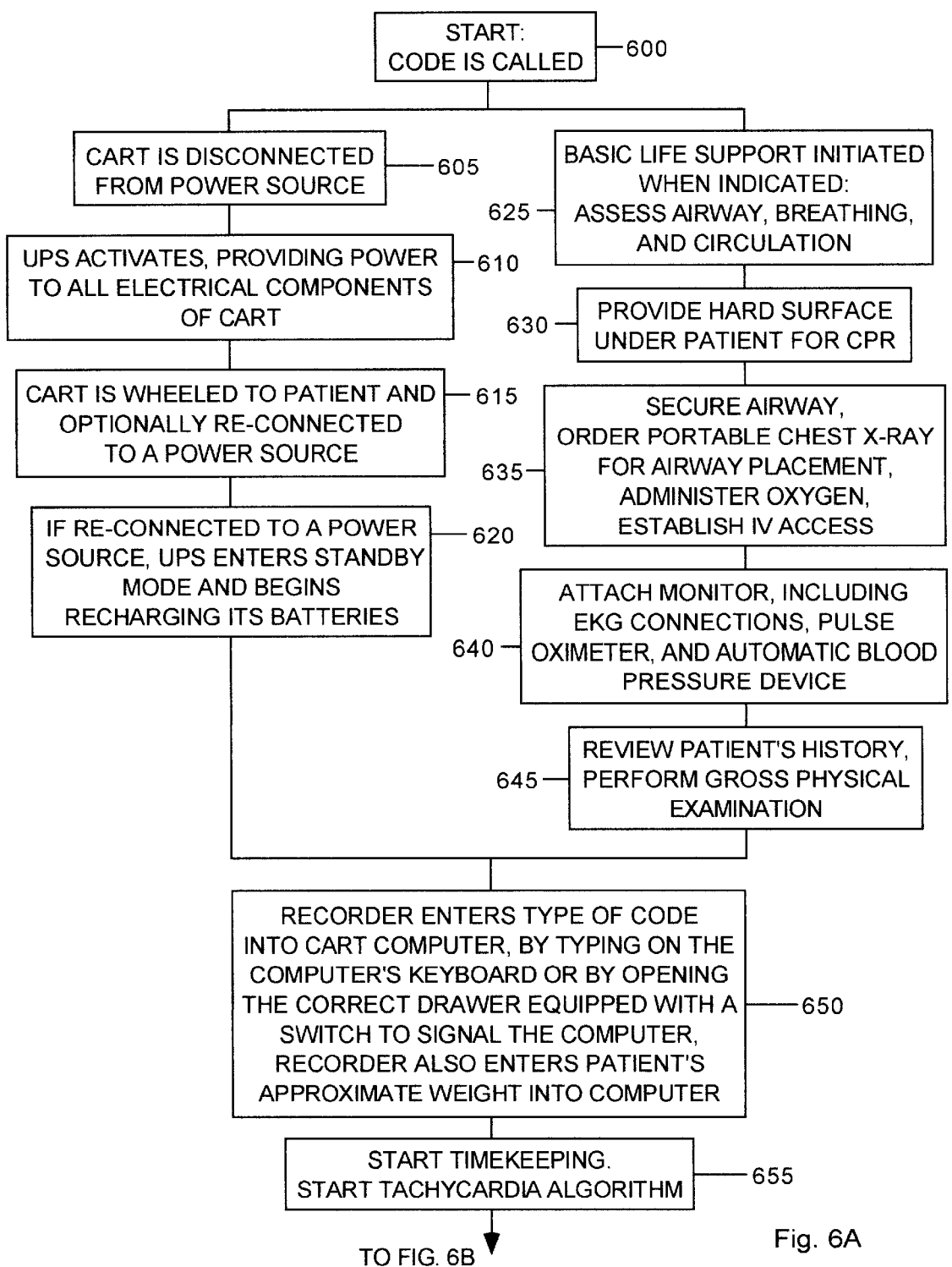
FIG. 6A is a flow chart depicting the flow of events in an exemplary ACLS algorithm for adult tachycardia.
Figure 6B:
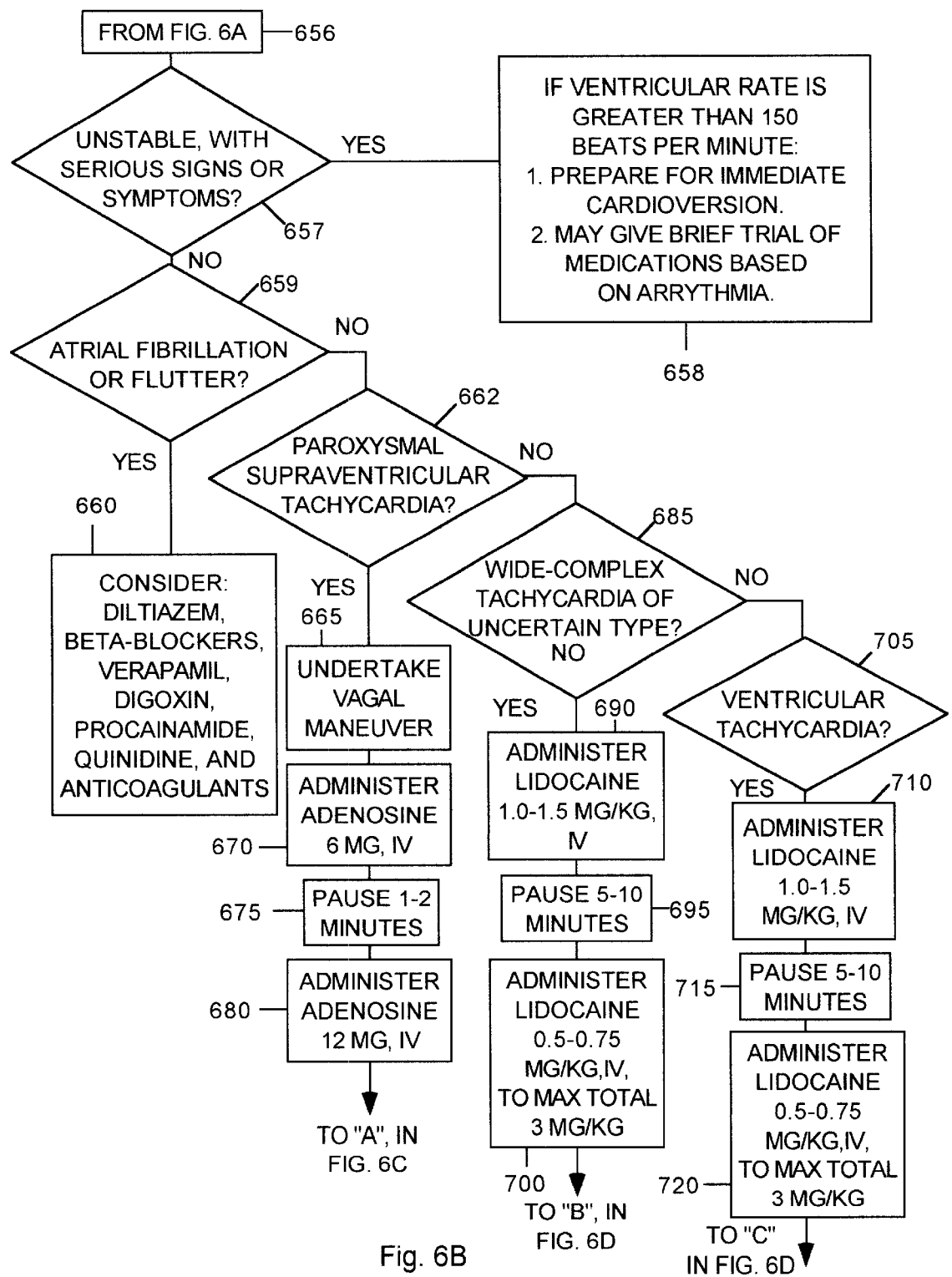
FIG. 6B is a flow chart depicting the flow of events in an exemplary ACLS algorithm for adult tachycardia.
Figure 6C:
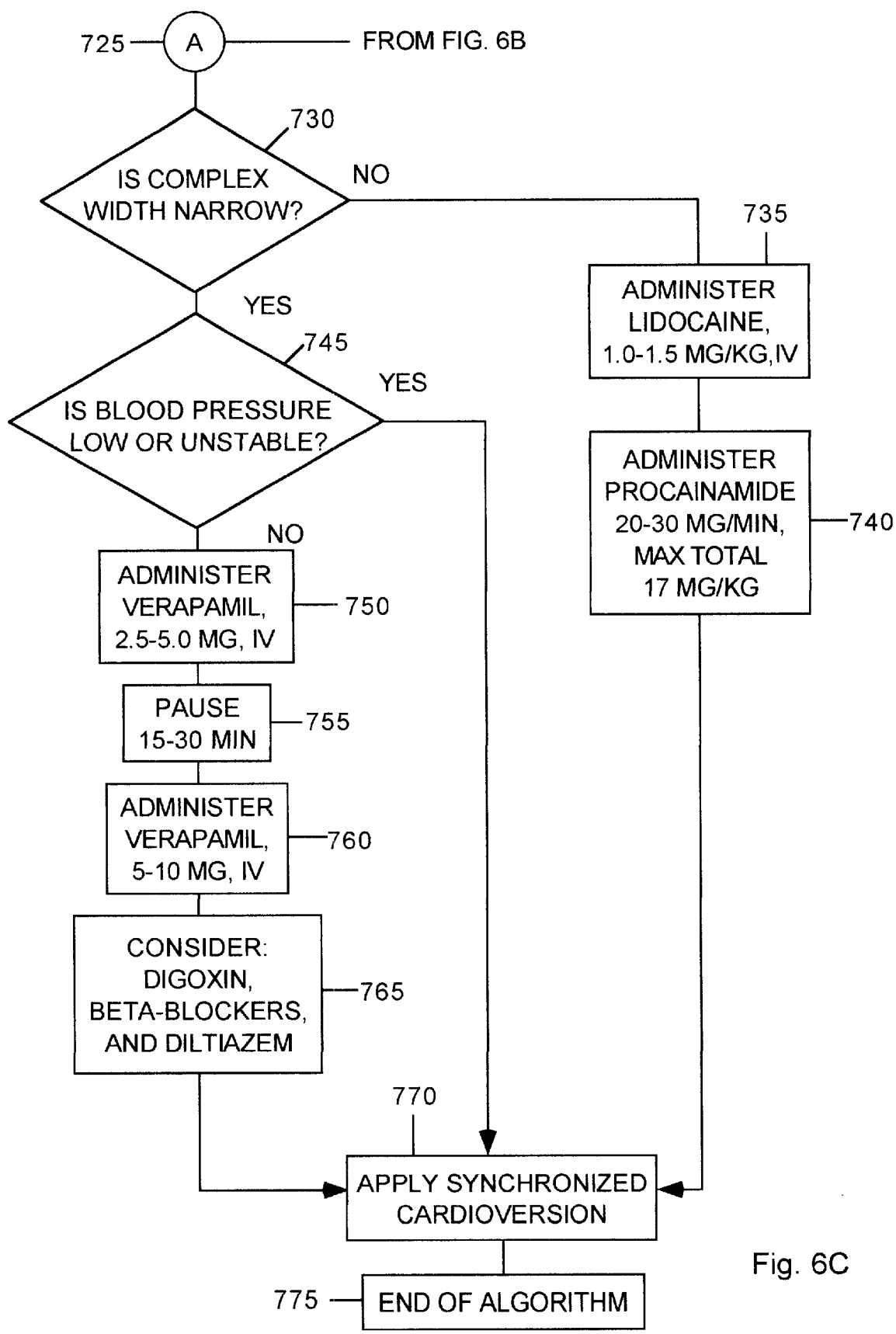
FIG. 6C is a flow chart depicting the flow of events in an exemplary ACLS algorithm for adult tachycardia.
Figure 6D:
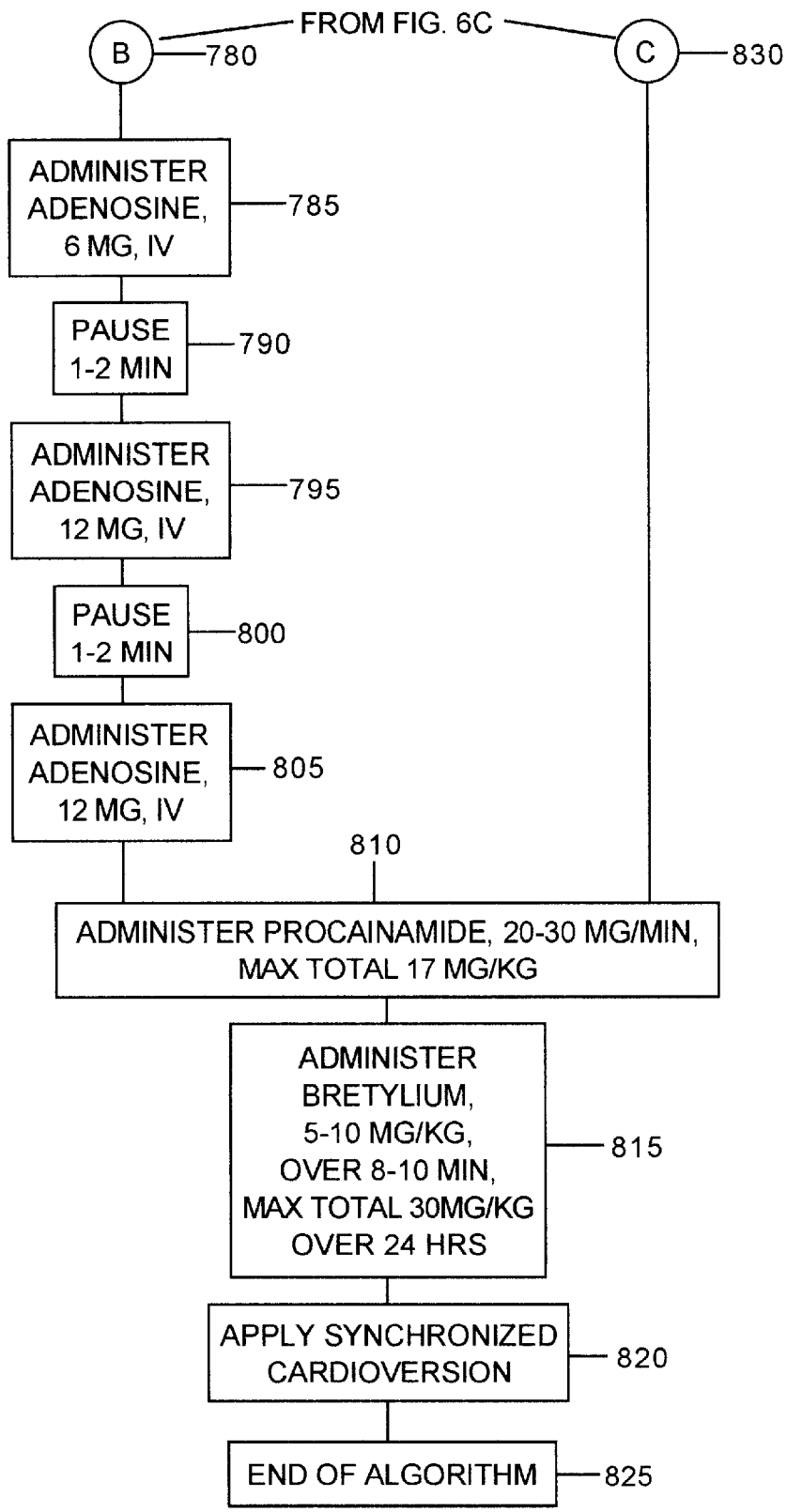
FIG. 6D is a flow chart depicting the flow of events in an exemplary ACLS algorithm for adult tachycardia.
Figure 7:
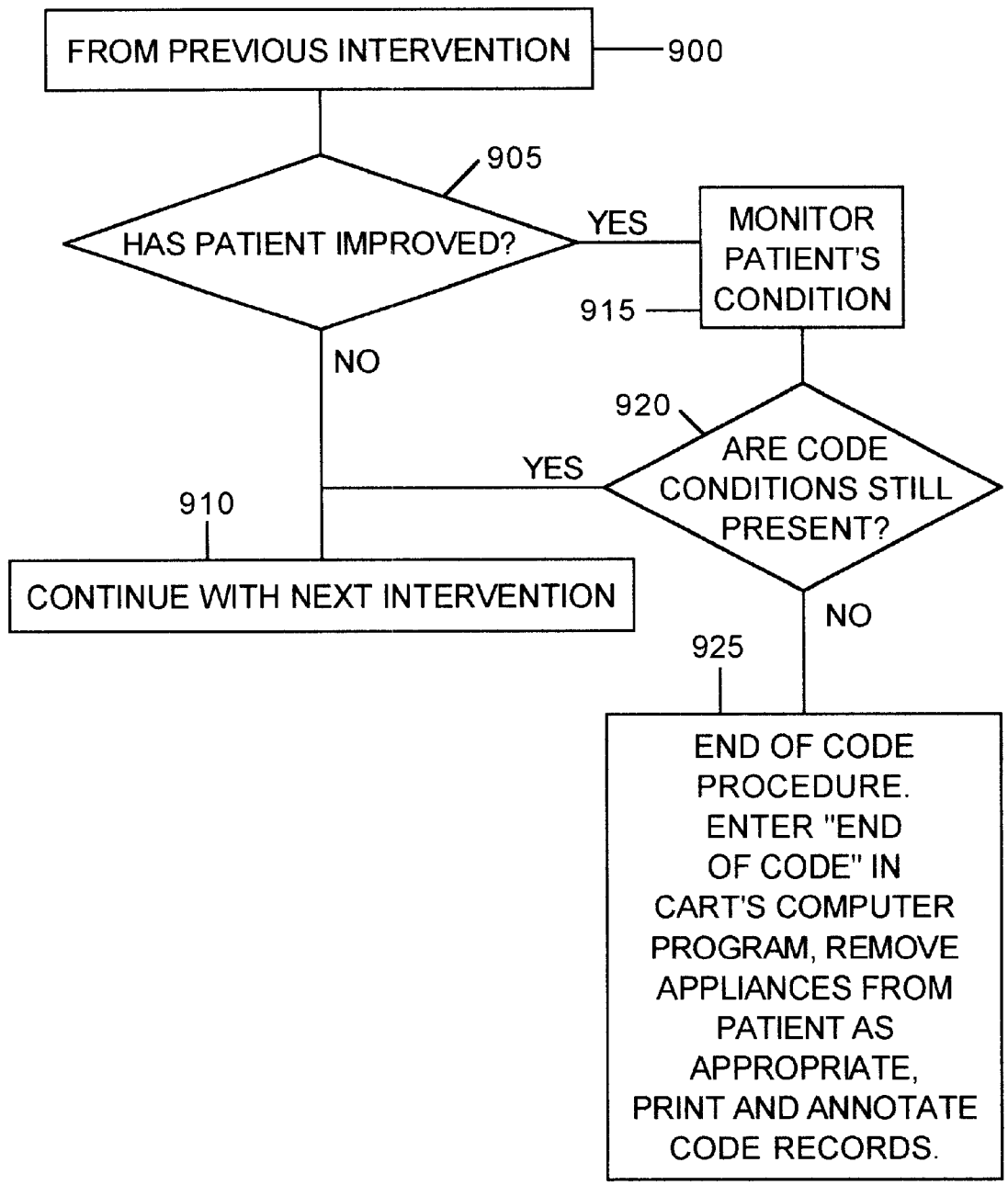
FIG. 7 is a flow chart showing events which are interspersed with those shown in FIGS. 6A through 6D.

An exemplar adult tachycardia code algorithm is shown in FIGS. 6A through 7. When a code is called (block 600), an emergency technician disconnects cart 100 (FIG. 1) from its main power source (block 605) and wheels it to patient 101. During this time, UPS 210 (FIG. 2) supplies power to all electrical devices on cart 100 (block 610). The capacity of the batteries in UPS 210 is normally sufficient to provide power to all instruments on cart 100 (FIG. 1) for the duration of a code, as long as 45 to 60 minutes. Optionally, UPS 210 can be plugged into a power source (block 615) during a code, at the discretion of the code personnel. In some cases this must be done because UPS 210 can only supply power for a limited period of time before its own batteries must be recharged. Once plugged in to an active power source, UPS 210 begins recharging its batteries (block 620).

In parallel with the above events, the code team assesses the patient's airway, breathing, and circulation, initiating basic life support functions if indicated (block 625). A hard surface, such as a back board 170 (FIG. 1), is placed under patient 101 to permit CPR (block 630). The patient's airway is secured, at first with a bag and mask (not shown) connected to oxygen tank 200 (FIG. 2), and subsequently by intubation, while intravenous access is also assured (block 635). The monitor functions of the cart are connected to patient 101 via leads 117 and 119 and tubing 118 which plug into connector 176 in cart 100 (block 640). These include EKG, pulse oximeter 142, automatic blood pressure monitor cuff 141, and the like. The patient's medical history is reviewed, and a gross physical examination is performed (block 645). With the completion of these steps, the main activity of the code continues.

At the patient's bedside, the recorder opens the drawer 130 appropriate to the kind of emergency code at hand (block 650). Switch 185 (FIG. 1) is activated and signals computer 175, identifying the code algorithm associated with drawer 130, in this case tachycardia. Alternatively, the recorder enters the type of code into computer 175 by typing it on keyboard 115. The proper code algorithm, in this example tachycardia, is displayed on monitor 150 of computer 175, and the program is run. Identification of the code algorithm is determined either by the code team or by the programming in computer 175. At this time, monitor screen 150 appears as shown in FIG. 8A. Computer 175 keeps a time record of all subsequent events. At the start of the code, the recorder also enters the patient's approximate weight into computer 175 by typing this information on keyboard 115. With this information, the calculator function in computer 175 calculates the proper dosage of medications to be given (block 655). The code algorithm has been selected and a prompt awaits entry of the patient's weight. After the patient's weight is entered, the contents of monitor screen 150 change to those shown in FIG. 9A. The code algorithm is shown at the top of screen 150. Below the code algorithm is the EKG followed by the patient's pulse rate, and a tracing of the most recent two or three seconds of heart rhythm. Next, the Blood Pressure (BP) readout is shown as the systolic pressure over the diastolic pressure. Then the pulse oximeter reading (OXY). The next line is for prompts and responses. The date and time are shown at the bottom of screen 150. Rhythm strip 140 is started by computer 175 and its appearance at this time is shown in FIG. 9B. In FIGS. 8A through 13B, signal amplitude is shown on the ordinate, and time is shown on the abscissa, as shown in FIG. 8B.

In addition to running the code algorithm, computer 175 interprets diagnostic information from the patient's EKG, pulse oximeter 142, blood pressure cuff 141, and any other source of data connected to the patient. Progress through the code is guided by this diagnostic information supplied by computer 175. For example, computer 175 may detect the presence or absence of a normal or abnormal EKG rhythm. If a normal sinus rhythm, normal blood pressure, and normal oxygenation are detected, it may be possible to terminate the code without further intervention. On the other hand, if the code is started because the patient experiences tachycardia, and at a later time the EKG reveals a different rhythm condition, a different code algorithm may be required. Monitor screen 150 on computer 175 will indicate this, a verbal message is issued by loudspeaker 116, and the emergency personnel can take appropriate action.

Although they are memorized by emergency personnel, the instructions in the algorithm (blocks 655 through 925) appear sequentially on monitor screen 150 as a reminder through the progress of the code.

Next, monitor screen 150 shows the prompt (block 657, FIG. 9A) "Unstable, with serious signs or symptoms?" If the answer is "yes", and if the ventricular rate, as shown by the EKG, is greater than 150 beats per minute, the algorithm offers two choices (block 657): (1) Prepare for immediate cardioversion, (2) May give brief trial of medications based on arrythmia (block 658). A prompt, indicating such as "CARDIOVERSION OR CONSIDER BRETYLIUM 50 mg" will appear on screen 150, as shown in FIG. 11A. The volume of medication proposed is based on the previously entered weight of patient 101. This prompt may also be given audibly via loudspeaker 116, if desired. If bretylium is withdrawn from cart 100, light 156 is illuminated by computer 175. When the dose is given, the recorder presses button 156 and computer 175 indicates this as shown in FIG. 12A. Meanwhile, the patient's pulse is as shown on screen 150 and rhythm strip 140. In this example, cardioversion was chosen. Under these conditions, cardioversion is proposed by the ACLS guidelines (block 658), so monitor screen 150 displays the warning message: "CARDIOVERSION: STAND BACK", shown in FIG. 10A. At the same time, loudspeaker 116 (FIG. 1) loudly issues the same warning. The defibrillating shock is then applied through leads 117, and the code continues. At this point, as well as after each following step in the algorithm, the steps in FIG. 7 are interposed. These are shown explicitly only once in this example, in order to save space and avoid repetition.

Refer to FIG. 7. After an intervention (block 900), the patient's condition is assessed (block 905). This assessment includes the patient's pulse, blood pressure, EKG, color, and any other factors the emergency team deems important. If the patient has not improved, the code continues with the algorithm (block 910). If the answer for block 905 is "yes", the patient's condition is monitored (block 915). If the conditions which initiated the code are still present (block 920), the code continues with the next intervention in the algorithm (block 910). The patient's condition during a code is usually ever-changing. For example, at one moment one type of heart rhythm may be present, and at another moment, a different heart rhythm may be present. The diagnostic capability of computer 175, with its various connections to the patient, helps guide progress of the code. If the code conditions are not still present, the code procedure is terminated (block 925). The recorder enters "End of Code" in the program in computer 175, and the various appliances, blood pressure monitor, EKG, etc., are removed from the patient as appropriate. The recorder then prints and annotates the records from the code.

If the head of the code team has determined that every effort to revive the patient has been exhausted, or the patient's family requests an end to attempts at revival, the time of cessation of code activity is evident on monitor screen 150 of computer 175 as a series of flat lines, i.e. there is no blood pressure, no respiration, no indication of pulse oximetry, and the like. The time at which all activity seen by computer 175 ceases serves to fix the time of the patient's death.

If, instead the patient's condition is not unstable with serious signs or symptoms (block 657), but the conditions for the code still persist, the next choice point is displayed on monitor 150 of computer 175. If atrial fibrillation or flutter is present (block 659), then a number of drugs may be considered (block 660). If atrial fibrillation or flutter is not present, then the algorithm moves to the next choice point. Is paroxysmal supraventricular tachycardia present (block 662)?

If, at this point, the emergency team withdrew the drug adenosine from its compartment in drawer 130 (FIG. 1), the program in computer 175 would note this departure from the tachycardia algorithm and issue an alarm. The alarm is either visual, on monitor screen 150, or audible or both. The next step in the algorithm is a vagal maneuver (coughing, holding one's breath). Although the withdrawal of adenosine from drawer 130 was contrary to the algorithm, light 156 on drawer 130 would illuminate under the control of computer 175, indicating that a medication is ready to be administered. If the adenosine container is replaced in its location in drawer 130, light 156 will go off and no record of its withdrawal will be kept. If, however, the adenosine is administered (block 670), the recorder will press button 155 and computer 175 will store this information for later printing of the record on paper 135.

If the patient's condition improves after the administration of adenosine (block 670), the code may be terminated according to the steps in FIG. 7. If the patient's condition does not improve, then more adenosine is administered (block 680), and the code continues.

If the patient was not experiencing paroxysmal supraventricular tachycardia (block 660), then block 685 or 705 may apply and the algorithm will continue down those paths.

If all else fails, synchronized cardioversion is applied (block 770). At this point, no further guidelines are available and the emergency team will rely on non-conventional measures to attempt to save the patient's life. The code will end when the patient recovers a life-sustaining rhythm or expires.

At the end of the code, the recorder enters this fact into computer 175 by typing "End of Code" on keyboard 115. Computer 175 then prints on paper 135 all information gathered during the code as a function of time. This information includes the patient's blood pressure, blood oximeter readings, heart rate, and any other data gathered during the code. The EKG rhythm strip 140 is also appended to the record on paper 135. Finally, the recorder or another member of the emergency team annotates these records as appropriate. At this point, the code is ended and the record is filed.

Computer 175 also keeps a record of the contents 305, 310, 315, 320, etc. of cart 100, providing an inventory of items used. Cart 100 is finally sent to a supply department for restocking.

In addition to preserving information about the progress of the code, the record indicates the success of various medications and interventions with the particular patient. This information can be useful in future emergencies with this patient, and possibly with others.

Figure 12:
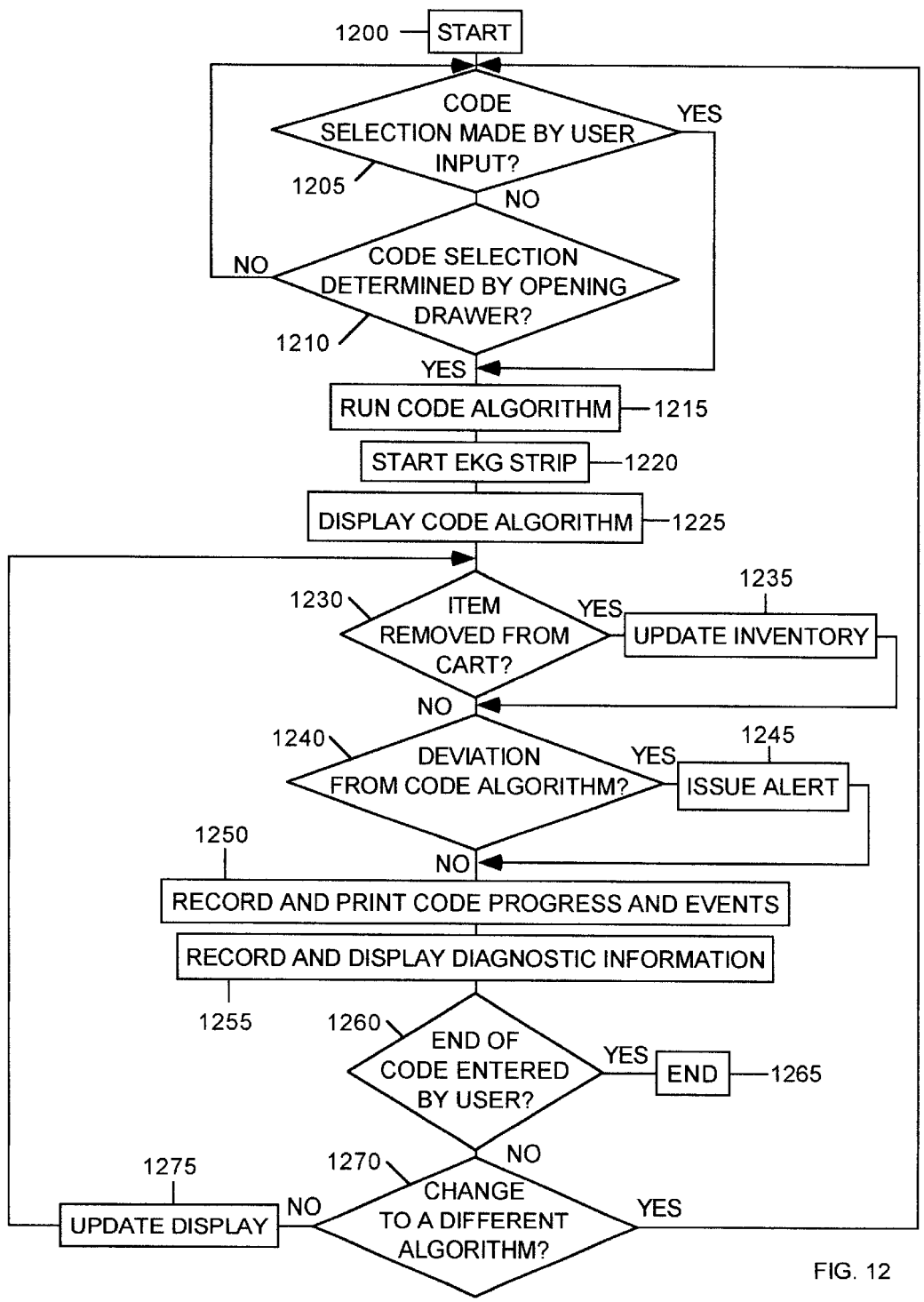
FIG. 12 is a flowchart showing the operation of the code cart system.

The operation of the code cart system is shown in FIG. 12. Before the start of a code, computer 175 (FIG. 1) awaits instructions, as indicated by blocks 1200, 1205, and 1210. The identity of a code algorithm to be used can be entered through keyboard 115 (FIG. 1) by a user (not shown), block 1205. When the user enters the code, the program immediately runs the selected code, block 1215. Alternatively, the code to be used may be selected by opening one of drawers 130 and having this action be detected by switch 185 (FIG. 1), block 1210.

After the code type is selected, execution of its algorithm begins immediately, block 1215. The EKG of patient 101 is recorded on strip 140 (FIG. 1), block 1220. The algorithm of the selected code is displayed on monitor 150, block 1225.

When an item is removed from cart 100, block 1230, as detected by sensor 400, or switch elements 500 and 505 (FIG. 3), the cart's inventory record in computer 175 is updated, block 1235. If no item is removed at this time, block 1230, progress continues to block 1240. If the removal of an item from cart 100 deviates from recommendations of the code, block 1240, an alert is issued, block 1245. Otherwise, progress continues to block 1250.

In block 1250, computer 175 records and prints the progress and events of the code. Diagnostic information is also recorded and displayed, block 1255.

The user or recorder may terminate the code at any time by entering an "end-of-code" command on keyboard 115 of computer 175, block 1260. If this is done, the operation of this computer program is halted, as indicated by "END" in block 1265.

The user may also elect to change to a different code algorithm as conditions require, block 1270. If this is the case, execution of the program returns to the top of block 1205 and continues from there.

If there is no change in code algorithm, the display on monitor 150 is updated, block 1275, and execution of the program continues from block 1230.

CONCLUSION, RAMIFICATIONS, AND SCOPE

Accordingly, an improved medical emergency code cart is provided. The new cart employs a computer, a computer program, and sensor mechanisms which operate in conjunction with predetermined emergency code algorithms. Patient care is improved and emergency team stress levels are reduced by guidance from the algorithms during the stressful period of a code. Prompts are provided on the cart's computer monitor screen and over its loudspeaker. Alarms are given when the computer detects deviations from a code algorithm, yet medical personnel are permitted to stray from the algorithm if they believe it is necessary for the patient's welfare. The progress of the code is documented accurately using a single time reference. A permanent record is printed. All medications and apparatus for a particular type of code are kept in a drawer which is labeled for that code. The organization of the contents of the drawer is standardized according to ACLS or other guidelines. This further reduces the possibility for error.

While the above description contains many specificities, these should not be construed as limitations on the scope of the invention, but as exemplifications of the presently preferred embodiments thereof. Many other ramifications and variations are possible within the teachings of the invention. For example, the cart can be larger or smaller, it can include more or fewer monitoring facilities, and its computer can be connected to a larger computer network so codes can be observed or directed remotely. Thus the scope of the invention should be determined by the appended claims and their legal equivalents, and not by the examples given.

I claim:

1. A medical code system, comprising:
   a housing;
   drawers in said housing;
   compartments in each of said drawers;
   sensors in respective compartments of each of said drawers for detecting presence of medical supplies in individual compartments; and
   a computer connected to said sensors, wherein said computer is arranged to:
      store a plurality of medical code algorithms;
      sequentially display instructions for a selected algorithm for guiding medical workers treating a patient during a code; and
      activate an alert when any of said medical supplies removed from any of said drawers is not indicated by said selected algorithm.

2. The medical code system of claim 1, wherein said computer is arranged to maintain an inventory record of said supplies.

3. The medical code system of claim 1, wherein said computer is arranged to maintain an inventory record of said supplies, update said inventory record when any of said medical supplies is removed from any of said drawers, and undo said update when said any of said medical supplies is replaced into said any of said drawers.

4. The medical code system of claim 1, wherein said computer is arranged to display a corresponding algorithm when a name of said corresponding algorithm is entered into said computer through an input device connected to said computer.

5. The medical code system of claim 1, further including medical equipment connected to said computer, wherein said computer is arranged to compare diagnostic information measured by said medical equipment with code conditions defined by said selected algorithm, and indicate that said code is terminated when said patient is outside of said code conditions.

6. The medical code system of claim 1, further including medical equipment connected to said computer comprising an electrocardiograph, a defibrillator, interfaces to a pulse-oximeter sensor, and an automatic blood pressure monitor cuff.

7. The medical code system of claim 1, further including open-drawer detection switches on respective drawers connected to said computer for detecting when each of said drawers is opened, wherein each of said drawers is associated with a different algorithm, and said computer is arranged to display a corresponding algorithm when each of said drawers is opened.

8. The medical code system of claim 1, further including supply location indicator lamps on respective drawers connected to said computer, wherein said computer is arranged to activate a corresponding supply location indicator lamp to alert said medical workers that a corresponding medical supply indicated by said selected algorithm is in a corresponding drawer.

9. The medical code system of claim 1, further including supply usage recording switches on respective drawers connected to said computer, wherein said computer is arranged to record usage of a removed medical supply when a corresponding supply usage recording switch is pressed.

10. A medical code system, comprising:
   a housing;
   drawers in said housing;
   compartments in each of said drawers;
   sensors in respective compartments of each of said drawers for detecting presence of medical supplies in individual compartments;
   electrical medical equipment on said cart for providing diagnostic information on a patient and applying interventions to said patient during a code; and
   a computer connected to said sensors and said medical equipment, wherein said computer is arranged to:
      store a plurality of medical code algorithms;
      sequentially display instructions for a selected algorithm for guiding medical workers treating said patient;
      display diagnostic information measured by said medical equipment; and
      chronologically record usage of said medical supplies, usage of said medical equipment, said diagnostic information, and interventions applied to said patient.

11. The medical code system of claim 10, wherein said computer is arranged to activate an alert when any of said medical supplies removed from any of said drawers is not indicated by said selected algorithm.

12. The medical code system of claim 10, wherein said computer is arranged to maintain an inventory record of said supplies.

13. The medical code system of claim 10, wherein said computer is arranged to maintain an inventory record of said supplies, to update said inventory record when any of said medical supplies is removed from any of said drawers, and undo said update when said any of said medical supplies is replaced into said any of said drawers.

14. The medical code system of claim 10, wherein said computer is arranged to display a corresponding algorithm when a name of said corresponding algorithm is entered into said computer through an input device connected to said computer.

15. The medical code system of claim 10, wherein said computer is arranged to compare diagnostic information measured by said medical equipment with code conditions defined by said selected algorithm, and indicate that said code is terminated when said patient is outside of said code conditions.

16. The medical code system of claim 10, wherein said medical equipment connected to said computer comprise an electrocardiograph, a defibrillator, interfaces to a pulse-oximeter sensor, and an automatic blood pressure monitor cuff.

17. The medical code system of claim 10, further including open-drawer detection switches on respective drawers connected to said computer for detecting when each of said drawers is opened, wherein each of said drawers is associated with a different algorithm, and said computer is arranged to display a corresponding algorithm when each of said drawers is opened.

18. The medical code system of claim 10, further including supply location indicator lamps on respective drawers connected to said computer, wherein said computer is arranged to activate a corresponding supply location indicator lamp to alert said medical workers that a corresponding medical supply indicated by said selected algorithm is in a corresponding drawer.

19. The medical code system of claim 10, further including supply usage recording switches on respective drawers connected to said computer, wherein said computer is arranged to record usage of a removed medical supply when a corresponding supply usage recording switch is pressed.

20. The medical code system of claim 10, further including a printer connected to said computer for printing a chronological record of usage of said medical equipment, usage of said medical supplies, and said diagnostic information measured by said medical equipment during said code.

21. A medical code system, comprising:
   a cart with wheels;
   drawers in said cart;
   compartments in each of said drawers;
   sensors in respective compartments of each of said drawers for detecting presence of medical supplies in individual compartments;
   electrical medical equipment connected to said computer and comprising an electrocardiograph, a defibrillator, interfaces to a pulse-oximeter sensor, and an automatic blood pressure monitor cuff; and
   a computer connected to said sensors and said medical equipment, wherein said computer is arranged to:
      store a plurality of medical code algorithms;
      sequentially display instructions for a selected algorithm for guiding medical workers treating a patient during a code;
      display diagnostic information measured by said medical equipment;
      activate an alert when any of said medical supplies removed from any of said drawers is not indicated by said selected algorithm; and
      chronologically record usage of said medical supplies, usage of said medical equipment, said diagnostic information, and interventions applied to said patient during said code.

22. The medical code system of claim 21, wherein said computer is arranged to maintain an inventory record of said supplies.

23. The medical code system of claim 21, wherein said computer is arranged to maintain an inventory record of said supplies, to update said inventory record when any of said medical supplies is removed from any of said drawers, and undo said update when said any of said medical supplies is replaced into said any of said drawers.

24. The medical code system of claim 21, wherein said computer is arranged to display a corresponding algorithm when a name of said corresponding algorithm is entered into said computer through an input device connected to said computer.

25. The medical code system of claim 21, wherein said computer is arranged to compare diagnostic information measured by said medical equipment with code conditions defined by said selected algorithm, and indicate that said code is terminated when said patient is outside of said code conditions.

26. The medical code system of claim 21, further including open-drawer detection switches on respective drawers connected to said computer for detecting when each of said drawers is opened, wherein each of said drawers is associated with a different algorithm, and said computer is arranged to display a corresponding algorithm when each of said drawers is opened.

27. The medical code system of claim 21, further including supply location indicator lamps on respective drawers connected to said computer, wherein said computer is arranged to activate a corresponding supply location indicator lamp to alert said medical workers that a corresponding medical supply indicated by said selected algorithm is in a corresponding drawer.

28. The medical code system of claim 21, further including supply usage recording switches on respective drawers connected to said computer, wherein said computer is arranged to record usage of a removed medical supply when a corresponding supply usage recording switch is pressed.

29. The medical code system of claim 21, further including a printer connected to said computer for printing a chronological record of usage of said medical equipment, usage of said medical supplies, and said diagnostic information measured by said medical equipment during said code.

* * * * *